United States Patent [19]
Yoder et al.

[11] Patent Number: 5,900,243
[45] Date of Patent: * May 4, 1999

[54] CONTROL OF INSECT PESTS

[75] Inventors: Jay A. Yoder, Pineville, La.; Richard J. Pollack; Andrew Spielman, both of Needham, Mass.

[73] Assignee: The President and Fellows of Harvard College, Cambridge, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/540,717

[22] Filed: Oct. 11, 1995

Related U.S. Application Data

[62] Division of application No. 08/160,050, Nov. 30, 1993, Pat. No. 5,484,599.

[51] Int. Cl.$^6$ ..................................................... A01N 25/04
[52] U.S. Cl. ......................... 424/405; 424/406; 424/407; 424/84; 514/739
[58] Field of Search ..................................... 424/405–408, 424/409, 410, 84; 574/739, 919

[56] References Cited

U.S. PATENT DOCUMENTS

| | | | |
|---|---|---|---|
| 3,220,921 | 11/1965 | Greenbaum et al. | 167/30 |
| 3,665,040 | 5/1972 | Ruegg et al. | 260/614 R |
| 4,214,909 | 7/1980 | Mawatari et al. | 106/16 |
| 4,626,528 | 12/1986 | McHenry | 514/119 |
| 4,775,534 | 10/1988 | Bartlett et al. | 424/410 |
| 4,855,133 | 8/1989 | Kamei et al. | 424/84 |
| 4,925,730 | 5/1990 | Yamada et al. | 428/305.5 |
| 4,933,371 | 6/1990 | Mink et al. | 514/739 |
| 4,983,390 | 1/1991 | Levy | 424/404 |
| 5,118,506 | 6/1992 | Eichoefer | 424/196.1 |
| 5,258,408 | 11/1993 | Steltenkamp | 514/625 |
| 5,662,914 | 9/1997 | Shoray et al. | 424/405 |

OTHER PUBLICATIONS

Shorey et al: J Chem. Etol 18(11) 1992 pp. 2131–2142.
Ohorey et al: Environmental Entomology 22(5) 1993 920–924.
Das et al Entomol. Exp. Appl. 1976, 20(2) 195–8.
Champsex et al. —Abbstract of EP499570 Aug. 19, 1992.
Sugawara et al. Agric. Biol. Chem. (1984) 48(2) 519–20.
E.K. Markell and M. Voge, In: *Medical Parasitology*, 1981, p. 288.
The Merck Index, 11th Edition, (S. Budavari, ed.) 1989, p. 977.
The Merck Index, 11th Edition, (S. Budavari, ed.) 1989, p. 449.
B. Holldobler and E.O. Wilson, "Communication," Chapter 7, pp. 245–249, 265–269, In: *The Ants* 1990.
J.A. Yoder et al., "An Ant–Diversionary Secretion of Ticks: First Demonstration of an Acarine Hormone" *J. Insect Physiol.* 39:429–35, 1993.
J.A. Yoder et al., "Secretion of Squalene by Ticks," *J. Insect Physiol.* 39:291–96, 1993.
L.R. Nault and M.E. Montgomery, "Ant–Aphid Association: Role of Aphid Alarm Pheromone," *Science* 192:1349–50, 1976.
R.B. Tesh et al., "Trans–beta–farnesene as a Feeding Stimulant for the Sand Fly *Lutzomyia longipalpis* (Diptera: Psychodidae)," *J. Med. Entomology* 29:226–31, 1992.
Y.T. Das and A.P. Gupta, "Non–Repellancy of Two Insect Growth Regulators with Juvenile Hormone Activity to *Blatella Germanica*, " *Ent. Exp. & Appl.* 20:195–98, 1976.

(List continued on next page.)

*Primary Examiner*—Neil S. Levy
*Attorney, Agent, or Firm*—Medlen & Carroll, LLP

[57] ABSTRACT

Compositions are described for repelling and killing insect pests, such as fire ants and mosquitoes. Methods for controlling insect pests are found useful when applied to surfaces. A method for controlling ants, preferably fire ants, uses compositions containing the secretion from the large wax glands of ticks.

2 Claims, 2 Drawing Sheets

OTHER PUBLICATIONS

R. Schoni, et al., "The Aggregation–Attachment Pheromone of the Tropical Bont Tick *Amblyomma Variegatum* Fabricius (Acari, Ixodidae): Isolation, Identification and Action of its Components," *J. Insect Physiology* 30:613–618, 1984.

R.T. Mason et al., "Sex Pheromones in Snakes," *Science* 245:290–93, 1989.

C. F. Fioravanti and A. J. MacInnis, "The In Vitro Effects of Farnesol and Derivatives on Hymenolepis Diminuta," *J. Parasitology* 62:749–55, 1976.

K. Matsumoto et al., "The Alarm Pheromone of Grain Mites and its Antifungal Effect," In: *Recent Advances in Acarology*, vol. I, pp. 243–249, 1979.

CONTROL OF INSECT PESTS

This application is a division of application Ser. No. 08/160,050, filed Nov. 30, 1993, now U.S. Pat. No. 5,484, 599.

This invention was made with government support from NIH grant Al 19693. The government has certain rights in the invention.

FIELD OF THE INVENTION

The present invention relates to a method for controlling insect pests, and in particular for controlling insect pests in an environmentally safe manner.

BACKGROUND OF THE INVENTION

Efforts to control insect pests have focused on methods of repelling and killing insects. Concerns are that any repellent compound be non-toxic to users, and preferably that it not be foul smelling, discoloring or staining. Additionally, concerns are that the method not be harmful to the environment or to non-target animals.

People respond to the bites and stings of arthropod pests in highly individual ways. For example, mosquitoes, fleas, and bedbugs trigger variable reactions. E. K. Markell and M. Voge, In: *Medical Parasitology*, 1981. Some people have only minor irritation, while others suffer painful allergic reactions that may be localized or systemic. Furthermore, previous contacts with a particular insect species may cause hypersensitive reactions in subsequent episodes.

The bites and stings of various arthropods are cause for concern not only because they are painful in and of themselves, but also because they are a means of transmission of diseases. For example, mosquitoes transmit malaria and ticks transmit lyme disease. There remains a need to protect against the bites and stings of aggressive insect pests.

In the southern United States, fire ants are an aggressive pest that annually cost some states hundreds of thousands of dollars for control efforts. The bite and sting of the fire ant is extremely painful. The burning sensation can last for up to 24 hours and following that, pustules can form, taking up to ten days to heal. Additional problems may occur if the sting becomes infected. For individuals who are particularly sensitive to the venom, a single sting can cause shock and respiratory failure.

Fire ants also attack livestock. Small animals, such as birds and mammals, have been killed by fire ant stings. Further, the ants can cause crop damage by feeding on young plants. In Florida, fire ants attack young citrus trees, causing serious economic damage.

Fire ants cause further problems because of the huge mounds they build in the soil. The mounds may reach a height of two feet and a diameter of two to three feet. These large mounds contain up to 200,000 ants. Mounds in the field may be of such large size as to become obstacles for and cause damage to mowers and farm machinery. The ants infest fields, pastures and lawns.

Attempts to control fire ants may involve drenching the mounds with pesticides. However, this method introduces toxic chemicals into the environment and often results in overapplication of the pesticide. Furthermore, eradication of individual mounds is not completely effective since smaller colonies of ants may be hidden by foliage and serve as a source for reinfestation.

Various chemical formulations have been devised to control these pests. U.S. Pat. No. 3,220,921 issued Nov. 30, 1965 to Greenbaum and Weil discloses the dimer of hexachlorocyclopentadiene, also known as Mirex. Mirex shows pronounced toxicity to fire ants when ingested, although it has low insecticidal activity with mere contact. However, Mirex has been banned in the U.S. because evidence points to its being a potent carcinogen. See The Merck Index, 11th Edition, 1989, p. 977.

Use of baits is an alternative method of controlling fire ants. When toxic pesticides are mixed with bait, the worker ants carry the bait back to the colony as food. Amdro is one such bait product that contains a slow acting poison. Although the colony will eventually be destroyed, baits are slow working; they may take up to a month to be effective. Amdro is not for use on food crops.

Chemical repellents that have low toxicity for humans may be applied to the body. Mosquito repellents that are topically applied are common. Many of the useful insect repellents are tertiary amides. Among these, an all purpose insect repellent is N,N-diethyl-m-toluamide, also known as "DEET." Notwithstanding its low toxicity, it is an irritant to eyes and mucous membranes, and ingestion can cause CNS disturbances. See The Merck Index, 11th Edition, 1989, p. 449.

What is needed are compositions that repel or kill insect pests and can be applied to the locus where insect pests are found. Such compositions need to be safe for plants and animals that come into contact with the compositions. There is a further need for compositions that prevent insects from biting and stinging. The compositions need to be non-carcinogenic, non-irritating, and non-toxic to users.

SUMMARY OF THE INVENTION

The present invention relates to a method for controlling insect pests, and in particular for controlling insect pests in an environmentally safe manner. Compounds are described to be used alone and in combination with carriers and the like. Carriers are defined as substances that can be mixed with active insect controlling compounds to provide a medium for dispersement. Carriers may be solid or fluid. Solid carriers include powders. Bait herein refers to carriers that are insect attractants.

Control of insect pests is broadly defined as killing or repelling the pests. Repelling can refer to inhibiting aggressive activity including biting and stinging. Repelling additionally can refer to causing the pests to turn away. In this respect, applying a repelling composition to a surface causes the pests to avoid that surface. With respect to killing insects, an amount of a compound or composition sufficient to kill insects is an insecticidal amount. A compound that controls insect pests is an insect controlling compound.

The present invention provides a composition for killing insect pests comprising a mixture of an insecticidal amount of farnesol and a bait. In one embodiment the composition is a fluid. In an alternative embodiment the composition is a solid. In one embodiment the insect pest is ants and preferably fire ants. In an alternative embodiment the insect pest is mosquitoes.

In another embodiment the invention provides a method for killing insect pests comprising contacting a surface with an insecticidal amount of farnesol. In one embodiment the farnesol is in a fluid solution. In an alternative embodiment the farnesol is in a solid composition. Preferably, the composition comprises farnesol and a bait. Alternatively, the composition comprises farnesol dispersed in a powdered carrier. The method of the invention provides for killing ants and preferably fire ants. Alternatively, the method of the invention provides for killing mosquitoes. The surface contacted may be human skin.

The present invention also contemplates a method for controlling insect pests comprising contacting a surface with squalene. The surface may be human skin. In one embodiment the squalene is in a fluid solution. In an alternative embodiment the squalene is in a solid composition which may comprise squalene dispersed in a powdered carrier. In one embodiment of the invention the insect pests are ants and preferably fire ants.

The present invention also contemplates a method for controlling ants comprising contacting a surface with the secretion from the large wax glands of metastriate ticks.

While the invention envisions compounds for the control of a broad spectrum of insect pests, the invention is contemplated to be particularly suitable for controlling ants and mosquitoes.

DESCRIPTION OF THE INVENTION

Figure 1:
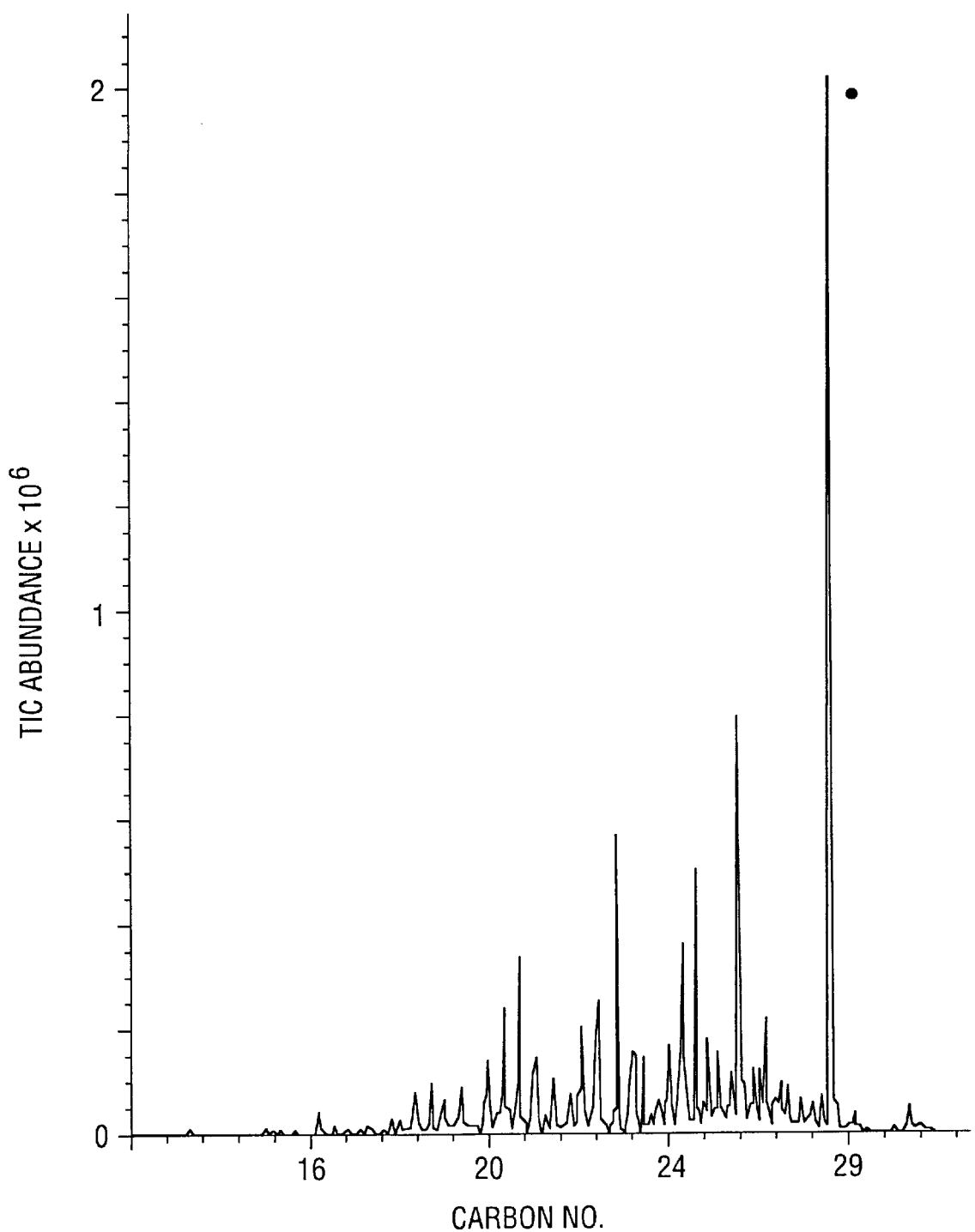
FIG. 1 shows total ion count (TIC) gas-chromatographic mass spectral analysis of the purified components of the large wax gland secretion of Dermacentor.

The present invention relates to a method for controlling insect pests, and in particular for controlling insect pests in an environmentally safe manner.

The present invention contemplates repelling insect pests by contacting a surface to be protected with secretory material from the large wax glands of metastriate ticks. The invention further contemplates repelling insect pests by contacting a surface with squalene (2, 6, 10, 15, 19, 23-hexamethyl-2, 6, 10, 14, 18, 22-tetracosahexaene, also known as Spinacene and Supraene). As a method for killing insects, the invention contemplates contacting a surface with farnesol (3, 7, 11 -trimethyl-2, 6, 10-dodecatrien-1-ol). The invention further contemplates contacting a surface with a combination of these compounds so that insects are repelled and thereafter, the insect dies.

Diverse chemical signals integrate the behavior of insects such as ants. For example, terpene compounds such as farnesenes serve as trail substance and recruitment pheromone of fire ants. Z,E-α-farnesene is the major recruitment pheromone laid down on trails, E,E-α-farnesene is a minor recruitment pheromone, Z,E-homofarnesene and Z,Z-homofarnesene are recruitment synergists, and a possible further role is attributed to Z,Z,Z-allofarnesene and n-heptadecane. Holldobler and Wilson, In: *The Ants* 1990. Other ants produce certain of these compounds and analogs (e.g. Myrmica, Monomorium, Daceton) and, as a result, recruitment pheromones of one species of ants cause responses in other species of ants that use the same or analogous compounds as their own recruitment pheromones. The nature of the fire ant response depends on the concentration of the pheromone; dilute product elicits an orientation response and concentrated pheromone elicits an alarm response.

Within the order Hymenoptera, there are numerous species of ants. Some representative species are *Pogonomyrmex badius, Acromyrmex octospinosus, Pristomyrmex pungens, Iridomyrmex humilis, Atta texana, A. rubropilosa, A. sexdens, A. cephalotes, A. octospinosus, Manica rubida, Solenopsis invicta, Myrmica lobicornis, M. scabrinodis, M. ruginodis, M. rubra, Myrmicaria eumenoides, Harpagoxenus sublaevis, Myrmecia gulosa, Teiramorium caespitum, Daceton armigerum, Monomorium pharaonis, Oecophylla longinoda, Formica lugubris, F. subintegra, Acanthomyops claviger, Leptothorax acervorum, L. kutteri, Leptogenys diminuta, Polyergus breviceps, Orectognathus versicolor, Lasius fuliginosus, Tetramorium imporium,* and *T. caespitum*. The present invention contemplates controlling the behavior of ants that respond to farnesene-like compounds.

Fire ants attack and consume certain ticks. When disturbed by ants, metastriate ticks produce a waxy secretion from the "large wax glands," which are visible as large pores arrayed on their dorsolateral surfaces. J. A. Yoder et al., "Ant-Diversionary Secretion of Ticks: First Demonstration of an Acarine Hormone" i J. Insect Physiol. 39; 429–435 1993. The product of the large wax glands of Dermacentor ticks is rich in squalene. (Yoder, J. A. et al.,"Secretion of Squalene by Ticks" *J. Insect Physiol.*39:291–96, 1993). The product of the glands appears to play a role in protecting the ticks from predatory fire ants since it appears to modify the aggressivity of fire ants.

The invention contemplates controlling ants by applying the secretion from the large wax glands of metastriate ticks to a surface. Alternatively, ants may be controlled by the application of squalene, a component of the large wax gland secretion, to a surface. The secretory compound or squalene may be formulated with known insecticides so that after the repellent effect is lost the treated area will not be safe for insects.

The insect control compounds are applied to surfaces of areas, structures or items to be made clear of insects, either by direct application of the compound in a liquid solution or dispersion, or dispersed in a powdered carrier or in a detergent composition. For example, an insecticidal amount of farnesol can be mixed with a carrier.

The invention contemplates a method for killing insect pests by applying a composition comprising farnesol to a locus containing the insect pest. The method of the invention is well suited for killing fire ants. Application of the composition may be by contacting the fire ant mounds with farnesol in a fluid solution. Contacting the fire ant mounds may be, for example, by injecting into, drenching, pouring, or spraying the mounds with the composition.

In one embodiment, compositions of this invention are an insecticidal amount of farnesol with bait. The composition of the present invention can be a mixture of an insecticidal amount of farnesol with any conventional attractant for insects, and particularly fire ants. Suitable attractants include soybean oil, peanut oil, corn oil, other vegetable oils, sugar, and other food attractants for the fire ants such as peanut butter, honey, etc. and conventional termite attractants such as brown-rot fungus, *Lenzites trabea*, impregnated in wood.

The bait compositions can comprise the toxicant of the present invention plus an effective amount of the attractant material and also may, if necessary, include a non-repellent carrier, such as corn cob grits, defatted corn cob grits, degermed corn cob grit, extruded corn pellets, etc. Typically, however, the bait will include 5 to 40 and preferably 10 to 30 percent by weight of the attractant material and 60 to 95 percent and preferably 70 to 90 percent by weight of a carrier. The bait should be placed in the field in an amount sufficient so that control is achieved. The amount of bait can vary widely depending on the degree of infestation. Typically from 0.5 to 5 pounds of bait should be placed per acre with each pound of bait containing between 0.1 and 10 grams of toxicant compound.

The following examples serve to illustrate certain preferred embodiments and aspects of the present invention and are not to be construed as limiting the scope thereof.

In the examples, the following abbreviations apply: h (hours); min (minutes); °C. (degrees Centigrade); $\mu$l (microliter); $\mu$g (microgram); cm (centimeters); mm (millimeters); $X^2$ (Chi squared value); RH (relative humidity); Fisher (Fisher Scientific, Pittsburgh, Pa.); Sigma (Sigma Chemical Co., St. Louis, Mo.); Waters (Waters Assoc., Milford, Mass.); H-P (Hewlett-Packard, Avondale Pa.); Zoecon (Zoecon Corp., Palo Alto, Calif.); J&W (J&W Scientific, Folsom, Calif.).

It is not intended that the present invention be limited by the particular methods used in the examples. The active compounds may be applied to surfaces alone or in combination with other materials. They may be applied directly to the surface of, for example, structures, objects, or the ground. They may be mixed with other components in the form of powders, pastes, solutions or bulk solids to be applied over a surface or they may be injected or otherwise applied under a surface, as, for instance, in introducing a solution into fire ant mounds.

EXAMPLE 1

Wax Gland Secretion Of Ticks

Ixodid ticks of the following kinds were used in this experiment: *Amblyomma americanum* (from Virginia), *A. maculatum* (from Texas), *Dermacentor andersoni* (from Montana), *D. variabilis* (from Virginia), *Ixodes dammini* (from Massachusetts), and *I. ricinus* (from Germany). Argasid ticks of the species *Ornithodorus moubata* and *O. parkeri* from colonies maintained in the laboratory were also examined. Ticks were maintained under a regimen of 14 h of light per day at 22–24° C. and 93% relative humidity in sealed chambers.

Forceps were used to gently pinch the legs of 15 nonfed adult females of each of the eight species. The legs of all such ticks were immediately retracted and the ticks became motionless. Droplets of fluid were produced from the dorsal margin of the scutum located just above the base of the stimulated leg of all metastriate ticks (Amblyomma spp and Dermacentor spp), but no prostriate (Ixodes spp) or argasid (Ornithodorus spp) ticks. The secretion appeared to flow from the ticks' dorsolateral surface just above the stimulated leg. Following bilateral disturbance of the legs, fluid seemed to burst from around the entire dorsum of the body and particularly from the lateral margins of the scutum. The secretion was volatile, evaporating within a few seconds and leaving a residual "sheen" over the surface of the tick. After about 10 min, the ticks extended their legs and began to crawl rapidly. Subadults, as well as adults reacted similarly to mechanical disturbance. These results show that in response to stimulation, metastriate ticks secrete a fluid having a volatile component. We refer to this as the secretion from the large wax glands.

Wax gland secretion in response to a natural predator was studied next. Specimens of the imported fire ant, *Solenopsis invicta*, were obtained from a colony maintained at Harvard University by E. O. Wilson, originally collected from Tallahassee, Fla. Ants were maintained under a regimen of 14 h of light per day at 22–24° C. Foraging worker ants were selected for the experiment. Where specified, prey were placed directly on the foraging arena of an ant colony.

Criterion for predation by ants was expressed as the proportion of prey that were "attacked" during 1 day of exposure. Ticks that were attacked by ants would be found dead and would have one or more appendages removed. Ticks were exposed to predator ants either in the ant colony or in petri dishes. For the latter, ticks were placed on a disc of white filter paper, together with 10 foraging ants and were enclosed in a sterile, polystyrene petri plate (100×15 mm) with 14 h of light, 22–24° C., and 93% RH.

Nonfed metastriate ticks (15 *D. variabilis* and 15 *A. americanum* of each sex) were gently placed in an ant colony by means of a camel's hair brush. Foraging ants that approached such a tick would sweep its body with their antennae, grasp it momentarily and generally invert the tick upon its dorsum. Ants were observed congregating on these ticks for up to 10 min. An inverted tick would remain immobile for a time, then extend its legs, right itself, and rapidly depart the site. Supplemental observations performed with the aid of a dissecting microscope established that the dorsolateral surfaces of free-ranging metastriate ticks secreted minuscule pulses of fluid when in contact with ants. Ants were never observed to bite or sting these ticks. Ticks survived in the ant colony for at least 4 days, as did similar ticks that were protected from predation by enclosure in mesh-covered vials.

Prostriate and argasid ticks (15 *I dammini* and 7 *O. moumata* of each sex) did not produce secretion when contacted by ants but they did retract their legs and become motionless. Ants invariably bit and stung them and gnawed their appendages from their bodies. All such ticks were killed within 1 day. In contrast, ticks that were protectively enclosed in mesh-covered vials survived in the ant colony for at least 3 days (Student's t-test P<0.05).

For comparison, ticks were placed into populations of the larval mealworm, *Tenebrio molitor*. All species of ticks were consumed by the mealworms. No protection of metastriate ticks was observed, as had been the case when ants were the predator. These results indicate that the wax glands of metastriate ticks secrete a composition that deters ants but not larval mealworms from predation of ticks.

EXAMPLE 2

Amount Of Secretory Material Available From Large Wax Glands

The amount of secretory material produced from the large wax glands was determined by measuring loss of body mass when the tick's legs were pressure stimulated. Ticks were gently lifted on a soft camel's hair brush and permitted to crawl onto the weighing pan of an electronic microbalance. After each was weighed, all of its legs were pressure stimulated until no more fluid was released. After the volatile element evaporated, the tick was reweighed. Metastriate ticks lost approximately 2% of their body mass. (Table 1.) Similarly-treated prostriate and argasid ticks, which do not produce secretions, remained constant in weight (ANOVA, P<0.05). Thus, loss of 2% of body mass of metastriate ticks, appears to represent the volatile material secreted from the large wax glands.

Determination of how rapidly the secretion of the large wax glands is replenished was determined by pressure-stimulating Dermacentor ticks until they had exhausted their secretion, and then stimulating them to exhaustion once again after various intervals of time. On initial stimulation, ticks lost 2% of their body weight (Table 2). When restimulated to exhaustion, it took 10 days for the ticks to lose 2% of their mass, once again. The relationship was constant, whether the ticks were held in a drying atmosphere (85%

RH) or a hydrating atmosphere (100% RH). Similar manipulation of Amblyomma ticks produced nearly identical results (data not shown). Thus, the secretion from the large wax glands of metastriate ticks is replenished within 10 days.

TABLE 1

Loss Of Weight Of Various Kinds Of Ticks
Following Pressure-Stimulation Of Their Legs

| | | Weight Of Tick (mg) | | | |
|---|---|---|---|---|---|
| | | Nonstimulated | | % Lost After Stimulation | |
| Kind Of Tick | Sex | Mean | SE | Mean | SE |
| Amblyomma | | | | | |
| americanum | male | 3.19 | 0.02 | 1.98 | 0.02 |
| | female | 6.14 | 0.03 | 2.01 | 0.03 |
| maculatum | male | 4.91 | 0.03 | 1.98 | 0.02 |
| | female | 9.43 | 0.03 | 2.03 | 0.02 |
| Dermacentor | | | | | |
| andersoni | male | 8.44 | 0.02 | 2.04 | 0.03 |
| | female | 10.67 | 0.03 | 1.96 | 0.02 |
| variabilis | male | 5.29 | 0.02 | 2.01 | 0.03 |
| | female | 6.31 | 0.03 | 2.05 | 0.02 |
| Ixodes | | | | | |
| dammini | male | 0.72 | 0.02 | 0 | — |
| | female | 1.54 | 0.03 | 0 | — |
| ricinus | male | 0.75 | 0.03 | 0 | — |
| | female | 1.72 | 0.03 | 0 | — |
| Ornithodorus | | | | | |
| moubata | male | 29.62 | 0.03 | 0 | — |
| | female | 38.83 | 0.03 | 0 | — |
| parkeri | male | 5.38 | 0.02 | 0 | — |
| | female | 7.17 | 0.03 | 0 | — |

Observations on each kind and sex of tick included 5 specimens and each was replicated until 15 different ticks were tested.

TABLE 2

Proportion Of Total Mass Lost Following Restimulation
Of Pressure-Stimulated, Weight-Synchronized, Female *Dermacentor variabilis* Ticks Maintained In Drying And In Hydrating Environments

| | Loss In Body Weight (%) At: | | | |
|---|---|---|---|---|
| Days From | 85% RH | | 100% RH | |
| Initial Stimulus | Mean | SE | Mean | SE |
| —* | 2.02 | 0.04 | 1.98 | 0.05 |
| 0 | 0 | — | 0 | — |
| 2 | 0.75 | 0.05 | 0.72 | 0.07 |
| 4 | 0.96 | 0.07 | 0.99 | 0.06 |
| 6 | 1.18 | 0.06 | 1.12 | 0.05 |
| 8 | 1.51 | 0.07 | 1.55 | 0.04 |
| 10 | 2.01 | 0.06 | 1.97 | 0.06 |
| 12 | 1.99 | 0.04 | 2.00 | 0.06 |

Observations represent the mean of 2 replicates of 3 ticks for each time point.
*Stimulated only once.

In another experiment the duration of protection from secretion-exhausted ticks was tested. Adult Dermacentor ticks were used as prey for ants. First, the legs of the ticks were pinched repeatedly with forceps, triggering secretion from the large wax glands. A prominent film of the waxy secretion flowed over the surface of the ticks. Pinching was continued until no more material was secreted in response. One day later, the secretion-depleted ticks were exposed individually (15 specimens of each sex) to foraging fire ants from the colony previously described. Within about 10 s, as many as 25 ants approached each tick. The ants covered the ticks but appeared not to sting them. Nonetheless, the tick survival in the ant colony was less than one day. Ticks that were similarly secretion-depleted but protected from predation by enclosure in mesh-covered vials survived the 3-day observation period of the experiment (Student's t-test, P<.0.05). Thus, although no stinging was observed when secretion-depleted ticks were first introduced into the ant colony, ant predation was not forestalled for a full day. Since the secretion that coated these ticks was not fresh but was one day old upon first exposure to the ants, an initial estimation of the duration of protection from the secreted material is between one and two days protection.

EXAMPLE 3

Purification Of Components Of The Wax Gland Secretion Of Ticks

To obtain samples of fluid released form the large wax glands of Dermacentor ticks, the legs of 8 nonfed, female ticks were repeatedly pinched with forceps and the resulting droplets of fluid were collected from the dorsum of the tick into drawn glass capillary tubes. Each sample was eluted with HPLC-grade chloroform:methanol (2:1, v/v) concentrated to 100 $\mu$l using a stream of nitrogen gas, passed through a silica gel column (Waters), and eluted with chloroform:methanol (2:1, v/v). The column was pretreated with two column volumes of solvent and the tick exudate was eluted with three column volumes of solvent The eluate was taken to dryness with nitrogen and reconstituted with 50 $\mu$l dichloromethane.

Efficiency of this extraction procedure was evaluated by ascertaining how efficient it was in the recovery of lipids from 2 mg of a commercial lipid preparation (Sigma) containing cholesterol, diverse fatty acids, triglycerides and wax esters. The commercial preparation was 96% recovered. Thin layer chromatography of the recovered commercial preparation showed it contained all the component lipids present before extraction (TLC solvent system 60:40:1 v/v/v, hexane:diethyl ether:acetic acid, detection with iodine vapor). This indicated that the extraction procedure was satisfactory for purifying lipids of large wax gland secretion.

A 0.4 $\mu$l sample of the extracted large wax gland secretion was injected for analysis by combined gas chromatography-mass spectroscopy based on electron-impact (H-P 5890-5970) using a DB-5 capillary column, (30 m length×0.25 i.d.) with a 0.25 $\mu$m coating (J&W Scientific). Carrier gas was helium flowing at 1 ml/min. Temperature was programmed for elevation from 75° C. to 150° C. at 20° C. /min and then to 290° C. at 8° C./min. For comparison, n-alkane standards (Sigma), various terpenoids including farnesol (Sigma, Cat. No. F 8627), squalene (Sigma, Cat. No. S 3626), and methoprene (Zoecon), and "golden oil" extract of Cecropia abdomens (C. M. Williams, Harvard University) were similarly analyzed. Log elution time was correlated with carbon number by injecting known hydrocarbon standards (y=0.51+0.031x, R=1.00).

Gas chromatographic analysis showed that one component dominated the mixture, comprising at least a quarter of its total nonvolatile mass (calculated by integrating the area in the tracing covered by each "peak") (FIG. 1). The retention time of this peak was 24.3 min, corresponding to a saturated n-alkane, 29 carbons in length (retention time of 25.0 min), or of standard squalene (retention time of 24.4 min). The retention times of other standards tested were: farnesol (2 isomers)—11.6 and 11.9 min, C. M. William's mixture (containing diverse juvenile hormone isomers)—
12.4–14.0 min and methoprene—16.0 min. The co-retention time of the predominant molecule of the wax gland secretion with a commercial squalene standard suggested that the large peak in the tracing may represent squalene (2, 6, 10, 15, 19, 23-hexamethyl-2, 6, 10, 14, 18, 22-tetracosahexaene).

Figure 2A:
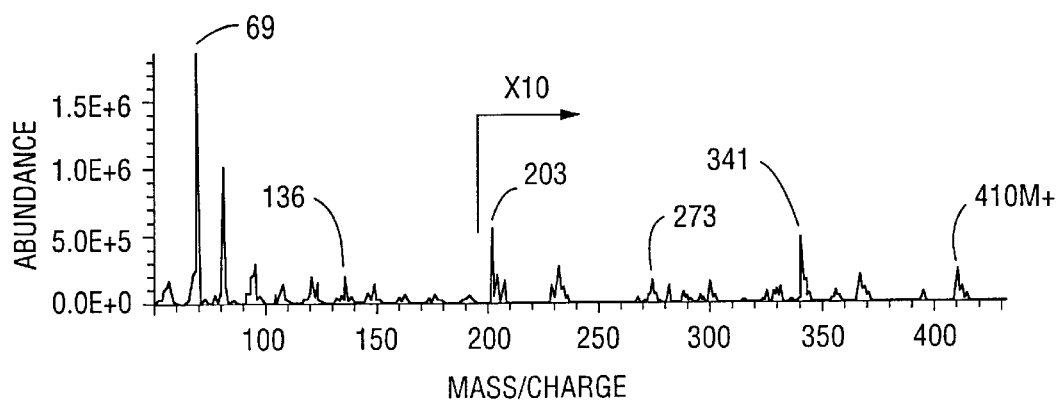
FIG. 2A shows mass spectroscopy analysis of a major component of the large wax gland secretion of Dermacentor.
Figure 2B:
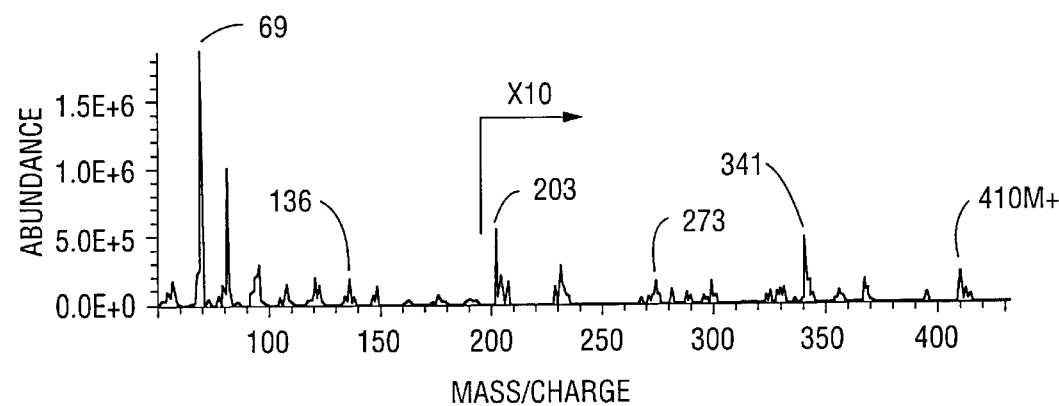
FIG. 2B shows mass spectroscopy analysis of squalene.

To define the structure of this molecule, the mass spectrum of the dominant peak of harvested secretion (FIG. 2A) was compared to that of a commercial sample of squalene (FIG. 2B). These spectra were identical. The resulting base ion mass/charge (m/z) of 69 is characteristic of acyclic terpenes and arises by allylic cleavage of the terminal isopentenyl group. The molecular ion (M+) at m/z 410 is equivalent to the formula weight of the commercial squalene standard. The six isoprene units comprising the parent molecule were characterized by the fragments m/z 341, 273, 203, 136 and 69. Other components of the secretion included branched and straight chain alkanes as characterized by base ions at m/z 57, and a series of fragments with 14 amu intervals. Retention times of standard hydrocarbons suggest that the minor components of the secretion range between $C_{16}$ and $C_{28}$. These data show that the dominant component of the secretion that flows from the large pores of pressure-stimulated Dermacentor ticks is squalene.

EXAMPLE 4

Protection Of Susceptible Prey By Exogenous Wax Gland Secretion

Secretory material from the large wax gland of Dermacentor ticks was harvested by pinching the legs of the tick while simultaneously holding a micropepette against the margin of the scutum. The material collected was used to coat Dermacentor ticks that had been secretion-depleted by forceps-stimulation the previous day. Ticks were placed on a disc of white filter paper, together with 10 foraging ants from the colony previously described and were enclosed in a sterile, polystyrene petri plate (100×15 mm). Ants attacked secretion-depleted ticks without the exogenous coating. However when 1 μl of freshly harvested secretion was applied topically, the secretion-depleted ticks were protected for the one-day duration of this experiment ($X^2$, P<0.05) (Table 3). Topical application of Dermacentor secretion to Ixodes

TABLE 3

Protection Of Allomone-Exhausted *Dermacentor variabilis* (DER) And *Ixodes dammini* (IXO) Ticks Against Predation By Fire Ants By Coating The Ticks With Allomone From Pressure-Stimulated *Dermacentor variabilis* Or With Terpenes

| | Secretion Of Large Wax Glands | | | | % Of Ticks | |
|---|---|---|---|---|---|---|
| | Harvested From | | Placed On | | Attacked By Ants | |
| | Kind Of | | Kind Of | | When Tick Was | |
| Treatment | Tick | Stage | Tick | Stage | Alive | Dead |
| Secretion | DER | female | DER | female | 40 | 100 |
| Secretion | DER | female | DER | male | 33 | 100 |
| Secretion | DER | male | DER | female | 33 | 93 |
| Secretion | DER | male | DER | male | 40 | 93 |
| None | — | — | DER | female | 93 | 100 |
| None | — | — | DER | male | 93 | 100 |
| Oil | — | — | DER | female | 100 | — |
| Oil | — | — | DER | male | 93 | — |
| Squalene | — | — | DER | female | 33 | 100 |

TABLE 3-continued

Protection Of Allomone-Exhausted *Dermacentor variabilis* (DER) And *Ixodes dammini* (IXO) Ticks Against Predation By Fire Ants By Coating The Ticks With Allomone From Pressure-Stimulated *Dermacentor variabilis* Or With Terpenes

| | Secretion Of Large Wax Glands | | | | % Of Ticks | |
|---|---|---|---|---|---|---|
| | Harvested From | | Placed On | | Attacked By Ants | |
| | Kind Of | | Kind Of | | When Tick Was | |
| Treatment | Tick | Stage | Tick | Stage | Alive | Dead |
| Farnesol | — | — | DER | female | 47 | 93 |
| Secretion | DER | female | IXO | female | 33 | 93 |
| Secretion | DER | female | IXO | male | 40 | 100 |
| Secretion | DER | male | IXO | female | 33 | 93 |
| Secretion | DER | male | IXO | male | 40 | 100 |
| None | — | — | IXO | female | 93 | 93 |
| None | — | — | IXO | male | 87 | 100 |
| Oil | — | — | IXO | female | 93 | — |
| Oil | — | — | IXO | male | 100 | — |
| Squalene | — | — | IXO | female | 33 | 100 |
| Farnesol | — | — | IXO | female | 40 | 100 |

Topically applied mineral oil was used for comparison. In each test, 1 tick was exposed to 10 ants for 1 day and was replicated 15 times.

ticks similarly protected them from ants. ($X^2$, P<0.05). Secretions were protective, regardless of the sex of the tick from which it was harvested. Male and female treated ticks were equally protected ($X^2$, P<0.05). Topical application of large wax gland secretion was ineffective, however, at deterring ants from feeding on ticks that had been killed by freezing. The results indicate that protection from topically applied wax gland secretion combined with mobility that effectuated escape from ant predators, prevented consumption of the live ticks by ants. With immobile, topically coated frozen ticks, the ants were able to maintain contact with the coated corpses, and the ants may have exhausted the coating within the interval of a day. These ablation rescue experiments show that the secretion is responsible for protecting ticks against ants.

Because squalene comprises about 25% of the mass of the waxy secretion of Dermacentor ticks, the ability of squalene to protect ant-vulnerable ticks from ant predation was examined. Also tested was the related terpenoid compound, farnesol, and mineral oil, which is not related in structure but which shares the physical characteristic with farnesol of being relatively viscous. One μl of squalene or farnesol was placed on the dorsum of either Dermacentor ticks that had been secretion-depleted the previous day or Ixodes ticks.

The results showed that either chemical protected the ticks as well as did corresponding applications of harvested large wax gland secretion (Table 3). Mineral oil was not protective ($X^2$, P<0.05). Similar results were observed when the chemicals were applied to each of 10 larval Tenebrio molitor mealworms (data not shown). Thus, 1 μl topical application of squalene or farnesol protect ticks and mealworm larvae from predation by ants.

In order to simulate the slow, droplet-size secretion produced by metastriate ticks in the presence of ants, capillary tubes containing 1 μl of test material were placed in the foraging arena of an ant colony. Ants responded similarly to the waxy secretion, squalene, farnesol, and another terpene, farnesene. Ants approached the test material, but soon retreated, averted their heads and groomed their antennae. Similar presentations of mineral oil and of distilled water elicited no apparent response. Filter papers (9 cm) streaked with 2 μl of test material were placed in the foraging arena of the ant colony. Ants piled trash on trails of the terpenoid compounds or of natural tick secretion but not on mineral oil or water trails. Although ants dutifully traced the course of farnesene trails, they followed trails formed by other terpenoids or by tick secretions less closely and did not respond at all to trails of mineral oil or water.

These results showed that the ants detected the presence of 1 $\mu$l and 2 $\mu$l doses of freshly harvested wax gland secretion, squalene, farnesol and farnesene and responded with a standard behavior. On the other hand 1 $\mu$l and 2 $\mu$l doses of mineral oil or water were either not detected or elicited no response.

EXAMPLE 5

Activity Of Tick Wax Gland Secretion And Terpenoid Compounds

In this experiment, workers of the fire ant, *Solenopsis invicta* Buren, were field-collected from Rapides Parish, La. In the laboratory, ants were grouped by 10 and housed in small plastic vials (5 cm length, 2.5 cm diameter) capped with mesh. Ants were exposed to a regimen of 14 hours of light per day, 22–24° C., and 93% relative humidity.

Field-collected (Rapides Parish, La.) nonfed female American dog ticks, *Dermacentor variabilis*, served as the source of natural tick wax gland secretion. To harvest the secretion, the ticks' legs were gently pinched by means of a forceps and the droplets of fluid that exude from the dorsolateral surface were drawn into a glass capillary tube. The fluid was tested at full strength.

Squalene and farnesol (Sigma) were diluted by 10% increments using HPLC-grade acetone (Sigma). Diluted preparations of the mineral oil, NUJOL, were used for comparison.

One $\mu$l of test material was drawn into a glass capillary tube (Fisher) and was then presented to a subcolony of 10 worker fire ants. The tube was held in the air with a droplet hovering just above the ants. The repellent activity of the test material was scored as $EC_{50}$, the concentration that was effective at preventing 50% of the test population from climbing up the tube (3 replicates of 15 tests each).

Fire ants approached a droplet of freshly harvested tick secretion, then immediately retreated. Ants reacted similarly to a droplet of squalene except that a few ants inspected the droplet of squalene with their antennae, then instantly retreated, averted their head and attempted to remove the material by grooming. The $EC_{50}$ of squalene was 60%. When droplets of farnesol or mineral oil were tested, 90% of the ants climbed up the tubes ($X^2$, P<0.05). The same results were obtained whether fresh or one year old samples of squalene, farnesol, or mineral oil were used.

Field tests of the compounds were made by mechanically opening a fire ant nest, producing a ground swarm of attacking worker and soldier ants. The various chemicals were drawn into glass capillaries and held just above the ants. Ants approached a droplet of fresh tick secretion and then immediately retreated. For the other chemicals, the laboratory observations held in the field.

These results showed that the fresh wax gland secretion and the squalene triggered an approach-then-retreat behavior in the ants while the mineral oil and farnesol each triggered an excited approach behavior.

EXAMPLE 6

Ant Repellent Activity Of Compounds Topically Applied To Mealworm Larvae

Fire ants were collected and maintained as described in Experiment 5. In the following experiment, mealworm larvae, *Tenebrio molitor*, in the final larval instar (mean length=22±3 mm) served as prey for the fire ants. In the laboratory, larvae were reared at 22–24° C., 93% relative humidity, under a light:dark cycle of 14L:10D. Unless otherwise noted, 5 $\mu$l of test material were applied topically to each test larva. Because larvae were of similar size, distribution of test material over the surface of each larva was relatively uniform. All larvae survived chemical treatments.

Fire ant attack was expressed as the proportion of 15 mealworm larvae that were bitten and stung. Upon attack, the larvae would roll, twisting their bodies in a "crazy-8" pattern. In the field, such movement recruited other ants to the site; the ants then removed the larvae into the colony. Field studies were conducted during late afternoon.

A 5 $\mu$l coating of tick secretion protected larvae from fire ant attack during the full five minute test duration (Table 4). However, topical application of squalene, farnesol, or mineral oil resulted in attack of mealworm larvae by fire ants before the end of the 5 min test duration. Squalene was more effective at delaying fire ant attach than farnesol, mineral oil, or acetone diluent ($X^2$, P<0.05) both in the laboratory studies and in field studies. Squalene-coated larvae were attacked by ants after about 3 minutes. A thicker application (range of 20–200 $\mu$l test substance per larva) did not enhance protection; ants preyed on larvae at the same rate whether in the laboratory or in the field.

The results using squalene-treated mealworm larvae suggested that squalene treatment offered short duration protection against attacking fire ants. As a parallel observation, 5 $\mu$l squalene applied to human fingers, followed by exposure to attacking fire ants resulted in the ants crawling onto the fingers and beginning to bite and sting after 4–5 minutes (5 replicates). Thus, the results showed that ants detected squalene at a 5 $\mu$l dose and responded to it in a characteristic manner, with a delay in the onset of aggressive behavior.

TABLE 4

Rate Of Predation By Fire Ants On Mealworm Larvae Coated With 5 $\mu$l Of Tick Secretion, Or Various Concentrations Of Squalene, Farnesol, Or Mineral Oil

| Treatment | Concentration | % Of Larvae Attacked By Ants In Minutes | | | | |
| --- | --- | --- | --- | --- | --- | --- |
| | | 1 | 2 | 3 | 4 | 5 |
| None | — | 100 | 100 | 100 | 100 | 100 |
| Tick allomone | undiluted | 0 | 0 | 0 | 0 | 0 |
| Squalene | Pure | 0 | 0 | 27 | 47 | 73 |
| " | 90% | 0 | 0 | 33 | 66 | 93 |
| " | 80% | 0 | 27 | 53 | 73 | 100 |
| " | 70% | 40 | 60 | 87 | 100 | 100 |
| " | 60% | 93 | 100 | 100 | 100 | 100 |
| " | 50% | 100 | 100 | 100 | 100 | 100 |
| Farnesol | Pure | 80 | 93 | 100 | 100 | 100 |
| " | 90% | 100 | 100 | 100 | 100 | 100 |

All of 15 oil- or acetone-treated larvae were consumed by ants within 1 min. Acetone served as the diluent. Each test exposed 1 mealworm larva to a sub-colony of 10 worker fire ants and was replicated 15 times. Field tests yielded nearly identical results.

EXAMPLE 7

Ant Toxicity Of Farnesol

Fire ants were collected and maintained as in Experiment 5. Mealworms topically coated with 5 $\mu$l of test material were offered to a subcolony of 10 worker fire ants housed in small plastic vials (5 cm length, 2.5 cm diameter). At a 5 $\mu$l dose, the ants behaved aggressively toward farnesol-coated larvae. Ants were less aggressive toward mineral oil-coated larvae. Ants ignored the squalene covered larvae upon initial exposure, however, after several minutes they resumed aggressive behavior. All ants enclosed in vials with farnesol-treated mealworms were found dead after one day (Table 5). Ants thrived in vials containing untreated, squalene-coated, or mineral oil-coated larvae ($X^2$, $P<0.05$).

To establish farnesol's limit of effectiveness, we determined the concentration that killed one half the test population. This point was reached when the concentration of farnesol was about 40%.

Testing was undertaken to determine whether the insecticidal effect of farnesol was tied to the aggressive biting and stinging behavior of the ants toward mealworms coated with farnesol. Aggressive behavior was eliminated by exposing subcolonies of fire ants merely to filter paper discs impregnated with 5 µl of various concentrations of farnesol diluted with acetone. The discs, were the size of the internal diameter of the vials, and were inserted into the bottom of the vials. All ants survived at all concentrations, even when pure farnesol was used (data not shown). Under these conditions, there was no indication that farnesol had been ingested by the ants since no farnesol-coated prey was available.

TABLE 5

Toxicity Testing Of Farnesol

| Treatment | Concentration (%) | % Of Ants Dead After 1 Day |
|---|---|---|
| None | — | 0 |
| Farnesol | pure | 100 |
| " | 90 | 100 |
| " | 80 | 100 |
| " | 70 | 100 |
| " | 60 | 90 |
| " | 50 | 80 |
| " | 40 | 50 |
| Squalene | pure | 0 |

Each test exposed a treated mealworm larva to a subcolony of 10 worker fire ants. Dilutions were made with HPLC-acetone. Treatments with oil, acetone, or ethanol were not toxic; all fire ants were found alive after 1 day (= d). Observations were replicated 5 times. Farnesol from a 1 year-old bottle produced nearly identical results.

The filter paper discs evenly and thinly disbursed the farnesol among the fibers of the paper whereas, when applied to ticks or mealworm larvae, farnesol remains as an oily coating. For this reason, tests were performed to determine whether a thin film of farnesol on a hard surface exhibits toxicity to ants. A 5 µl drop of farnesol was spread around the inner surface of a plastic storage vial. A subcolony of 10 worker fire ants was then introduced into the farnesol-treated vials. All ants were found dead within 4 h. Vials treated with squalene or mineral oil were not toxic ($X^2$, $P<0.05$). Vials coated with farnesol were effective fire ant killing chambers even after 4 days.

These results showed that only farnesol was toxic to ants and that toxicity was apparent whether or not accompanied by ingestion. Mere contact with farnesol in the form of an oily coating was sufficient to kill ants.

EXAMPLE 8

Toxicity Toward Mosquitoes

Farnesol and squalene were tested for toxicity toward the mosquito, *Aedes aegypti*. Containers capped with mesh screen housed 12 adult female mosquitoes. An initial placement of the containers on untreated skin confirmed that the mosquitoes would land and attempt to bite through the screen. Human subjects (N=7) applied pure squalene or farnesol (each at 50 µg/15.90 $cm^2$ of skin) to their forearms. They placed the screened end of the containers over the treated area for periods ranging from 15 seconds to 2 minutes. When placed on the treated area, neither squalene not farnesol were repellent to the mosquitoes. Mosquitoes landed on the treated skin and sometimes fed. Whether feeding or not, all mosquitoes that landed on farnesol-treated skin died within a day. In fact, over 50% died within 6 h. No toxicity was observed with squalene.

These results show that mosquitoes exhibit a toxic response to contact with farnesol. As demonstrated in this example, it is not intended that the invention be limited to controlling fire ants. Numerous species of ants are envisioned to be controllable by the method of the invention and, further, farnesol's toxicity extends beyond the order Hymenoptera. The capability for killing of insect pests is not intended to be limited by the demonstrated examples, rather, the species shown are representative species.

We claim:

1. A composition comprising:
   a) an insecticidal amount of farnesol applied to a surface as a viscous fluid film having a concentration greater than 60% and less than 90%; and
   b) a fire ant bait.

2. The composition of Claim 1 wherein farnesol is the sole insecticidal ingredient.

* * * * *